United States Patent [19]
Ebert et al.

[11] Patent Number: 5,981,476
[45] Date of Patent: *Nov. 9, 1999

[54] METHOD FOR TREATING BLADDER CANCER WITH A KEYHOLE LIMPET HEMOCYANIN COMPOSITION HAVING ENHANCED ANTI-TUMOR ACTIVITY

[75] Inventors: Ray F. Ebert, Derwood; Richard D. Swerdlow, Silver Spring, both of Md.

[73] Assignee: Perimmune Holdings, Inc., Rockville, Md.

[*] Notice: This patent is subject to a terminal disclaimer.

[21] Appl. No.: 09/009,121

[22] Filed: Jan. 20, 1998

Related U.S. Application Data

[63] Continuation of application No. 08/837,498, Mar. 26, 1997, Pat. No. 5,855,919, which is a continuation of application No. 08/343,808, Nov. 22, 1994, abandoned, which is a division of application No. 08/050,697, Apr. 19, 1993, Pat. No. 5,407,912.

[51] Int. Cl.$^6$ .................................................. A61K 38/16
[52] U.S. Cl. .............................. 514/8; 424/538; 424/547; 530/395
[58] Field of Search ................................ 514/8; 530/395; 424/538, 547

[56] References Cited

PUBLICATIONS

Markl, J. et al., *Chem. Abstract* 116:36518C (1991).
Markel, Juergen et al., *Chem. Abstract* 101:68045c (1984).
Harris, J.R. et al., *Computer Database Abstract* (1992).
Harris, J.R. et al., *Computer Database Abstract* (1992).
Senozan, Nail M. et al., *Chem. Abstract* 95:199291k (1981).
*Derwent Abstract* 89–179475/25, B04, STIE Dec. 17, 1987 (EP 320–528), and Search Report of EP 320 528.
Munder, P.G., *Chem. Abstract* 106:207290x (1987).
*Derwent Abstract* 88–008767/02, B04D16S03, INSP Jul. 7, 1986 (EP 252–829).
Annonymous, *Computer Database Abstract* (1987).
Gutterman, J.U. et al., *Computer Database Abstract* (1973).
Munder, P.G., *Present Status Non–Toxic Concepts in Cancer. Proc. Int. Symp.*, pp. 98–106 (1987).
Marsh, Christopher L. et al., *The Journal of Urology*, vol. 137, pp. 359–362 (1987).
Lau, Benjamin H.S. et al., *The Journal of Urology*, vol. 136, pp. 701–705 (1986).
Walsh, W.G. et al., *Urological Research* 11:263–265 (1983).
Calbiochem® Immunochemicals Product Information (1994–95).
Herskovits, T.T. et al., *Comp. Biochem. Physiol.* vol. 99B, No. 1, pp. 19–34 (1991).
Markl, J. et al., *Naturwissenschafen* 78:512–514 (1991).
Wu, C.Y., et al., *Chem. Abstract* 75:139026e (1971).
Savel–Niemann, Anette et al., *Invertebrate Dioxygen Carriers*, pp. 351–356 (1990).

(List continued on next page.)

*Primary Examiner*—Frederick Krass
*Attorney, Agent, or Firm*—William M. Blackstone

[57] ABSTRACT

The present invention is directed to a stabilized keyhole limpet hemocyanin (KLH) composition in which (i) its intact non-degraded subunit is approximately 400,000 in molecular weight based on SDS-PAGE analysis; and (ii) are contained at least about 50% didecameric or higher KLH multimers, based on sedimentation-equilibrium and/or sedimentation-velocity ultracentrifugation analyses. The KLH composition is stabilized at 4° C. by dissolving and storing it in an isotonic buffer preferably containing calcium and magnesium. It is critical that the KLH not have been frozen or lyophilized during its preparation or storage. The KLH composition demonstrates enhanced immunogenic activity, particularly enhanced anti-tumor activity, which is reduced if the KLH is frozen or lyophilized. The KLH composition of the present invention exhibits enhanced anti-tumor activity in a murine bladder tumor model and thereby represents a new and useful anti-tumor immunotherapeutic agent.

8 Claims, 6 Drawing Sheets

OTHER PUBLICATIONS

Vandenbark, Arthur A. et al., *Cellular Immunology* 60:240–243 (1981).
Herscowitz, H.B. et al., *Immunology*, 22:51–61 (1972).
Lamm, Donald L. et al., *The Journal of Urology*, vol. 149, pp. 648–652 (1993).
Olsson, Carl A. et al., *The Journal of Urology*, vol. 111, pp. 173–176 (1974).
Jurincic, Carlos D. et al., *The Journal of Urology*, vol. 139, pp. 723–726 (1988).
Lamm, Donald L. et al., *Urological Research*, 9:227–230 (1981).
Lamm, Donald L. et al., *The Journal of Urology*, vol. 128, pp. 1104–1108 (1982).
Ellerton, H. David et al., *Prog. BioPhys. Molec. Biol.* vol. 41, pp. 143–248 (1983).
Morales, Alvaro et al., *Urologic Clinics of North America*, vol. 19, No. 3, pp. 549–556 (1992).
Flamm, J. et al., *The Journal or Urology*, vol. 144, pp. 260–263 (1990).
Kälble, T. et al., *Urologe*, 30:118–121 (1991).
Flamm, J. et al., *British Journal of Urology*, 67:70–73 (1991).
Senozan, N.M. et al., *Invertebrate Oxygen–Binding Proteins*, pp. 703–717 (1981).
Itoku, Kendall A. et al., *Hematology/Oncology Clinics of North America*, vol. 6, No. 1, pp. 99–116 (1992).
Curtis, J.E. et al., *Clin. Exp. Immunol.*, 6:473–491 (1970).
Curtis, J.E., et al., *Clin. Exp. Immunol.*, 10:171–177 (1972).
Garvey, Justine S. et al., *Methods in Immunology*, pp. 135–139 (1977).
Herskovits, Theodore T., *Comp. Biochem. Physiol.*, vol. 91B, No. 4, pp. 597–611 (1988).
Herskovits, Theodore T. et al., *Comp. Biochem. Physiol.*, vol. 94B, No. 2, pp. 415–421 (1989).
Van Holde, K.E. et al., *Subunits in Biological Systems*, pp. 1–53 (1971).
Silverman, Debra T., et al., *Hematology/Oncolocy Clinics of North America*, vol. 6, No. 1, pp. 1–7 (1992).
Morales, A. et al., *The Journal of Urology*, vol. 116, pp. 180–183 (1976).
Lamm, D.L., *Eur. Urol.*, 21 (Suppl. 2):12–16 (1992).
Laemmli, U.K., *Nature*, vol. 227, pp. 680–685 (1970).
Van Holde, K.E. et al., *Biopolymers*, vol. 17, pp. 1387–1403 (1978).
Chodak, Gerald W. et al., *The Journal of Urology*, vol. 132, pp. 1032–1035 (1984).
Shapiro, Amos et al., *Cancer Research*, 43:1611–1615 (1983).
Pitzurra, L. et al., *Chem. Abstract* 96:18444q (1981).
Lamm, Donald L. et al., *Chem. Abstract* 96:15043x (1981).
Ford, Dennis et al., *Chem. Abstract* 98:3449n (1982).
Rong, Kangtai et al., *Chem. Abstract* 104:67135g (1985).
Van Tol, M.J.D. et al., *Chem. Abstract* 106:212066h (1986).

METHOD FOR TREATING BLADDER CANCER WITH A KEYHOLE LIMPET HEMOCYANIN COMPOSITION HAVING ENHANCED ANTI-TUMOR ACTIVITY

This application is a continuation of application Ser. No. 08/837,498, filed Mar. 26, 1997, now U.S. Pat. No. 5,855,919 which is a continuation of application Ser. No. 08/343,808, filed Nov. 22, 1994, now abandoned, which is a divisional of application Ser. No. 08/050,697, filed Apr. 19, 1993, now U.S. Pat. No. 5,407,912.

FIELD OF THE INVENTION

The present invention relates to a keyhole limpet hemocyanin (KLH) composition that has enhanced immunogenic properties, particularly enhanced anti-tumor activity. Specifically, the present invention relates to an immunogenic agent comprised of KLH formulated to contain >50% didecameric or higher KLH multimers that range in molecular weight from approximately 8–10 million. The immunogenic agent is useful as a cancer therapeutic agent and as an adjuvant or carrier protein.

BACKGROUND OF THE INVENTION

The publications and other materials used to illuminate the background of the invention or provide additional details respecting the practice are incorporated herein by reference numerals in parentheses, and for convenience are respectively grouped in the appended List of References.

For decades it has been known that hemocyanins are among the most potent of immunogens. Keyhole limpet hemocyanin (KLH; from the primitive gastropod mollusc, *Megathura crenulata*) has been among the most widely used and thoroughly studied of these (1–4). Thus, a single subcutaneous injection of KLH, without adjuvant, will elicit a strong antibody response in virtually 100% of animals, including humans.

There are a variety of well-known methods for purifying KLH, including differential centrifugation (5), gel-permeation chromatography followed by ion-exchange chromatography (2) and differential centrifugation followed by gel-permeation chromatography (6). Purified KLH that is commercially available typically has been either frozen or lyophilized after purification.

The solution structure of KLH and other mollusc hemocyanins has been studied extensively (7–10). Thus, it is known that KLH contains glycosylated polypeptide subunits with a molecular weight of 400–500,000 that assemble to form decameric (10-mer), didecameric (20-mer), and larger particles. These multimeric structures have been characterized by ultracentrifugation techniques that yield sedimentation coefficients of 11–19S for the dissociated subunits and 92–107S for the didecameric multimers (1,2). It is further known that a variety of factors may affect the size distribution of mollusc hemocyanins, including KLH (11,12). These factors include ionic strength, pH, temperature, $pO_2$, and the availability of certain divalent cations, notably calcium and magnesium.

Bladder cancer is the fourth most prevalent human malignancy, with about 49,000 new cases and 9,700 deaths reported annually (13). Whereas tumors in the bladder often can be removed by surgical resection, such treatment is not always curative. It has been reported that 50–80% of patients whose tumors have been surgically removed will develop recurrent invasive disease (14). Thus, there is a need for therapeutic approaches not only to treat the primary disease but also to prevent recurrent malignancies.

Morales and associates (15) were the first to describe successful treatment of bladder cancer by intravesicular (i.e., into the bladder) administration of an immunotherapeutic agent, Bacillus Calmette-Guérin (BCG). Extensive additional studies during the past 15 years have shown that both primary and recurrent bladder tumors are responsive to immunotherapeutic treatment modalities in general, and BCG treatment in particular (16,17).

KLH was first implicated as a potential immunotherapeutic agent for bladder cancer in studies by Olsson and associates (18) that disclosed a statistically significant reduction in the frequency of tumor recurrences in patients with low-stage bladder cancer who had received intradermal injections of KLH. Subsequently, other investigators have described human clinical trials in which KLH administered intravesically was effective in reducing the incidence of recurrent disease (19–21) or in treating primary tumors (22). The anti-tumor activity of KLH also has been demonstrated in an experimental animal model: the intralesional murine bladder tumor model of Lamm and associates (23–25). In this experimental model it has been observed that if the animals are not immunized subcutaneously with KLH prior to treatment, the anti-tumor activity was lost (25). Summarizing, KLH has been shown to have immunotherapeutic activity against bladder cancer, both in human clinical trials and in animal models.

Despite extensive literature and prior art regarding the structure and immunogenic and anti-tumor activity of KLH, there have been no studies that address the question of whether these two characteristics may be related or whether the immunogenic activity of KLH could be enhanced. Thus, it is an object of the present invention to enhance the immunogenic and anti-tumor activity of KLH.

SUMMARY OF THE INVENTION

The present invention is directed to a stabilized KLH composition in which (i) its intact non-degraded subunit is approximately 400,000 in molecular weight based on SDS-PAGE analysis; and (ii) are contained at least about 50% didecameric or higher KLH multimers, based on sedimentation-equilibrium and/or sedimentation-velocity ultracentrifugation analyses. The KLH composition is stabilized at 4° C. by dissolving and storing it in an isotonic buffer containing calcium and magnesium. It is critical that the KLH not have been frozen or lyophilized during its preparation or storage, as such treatment reduces its anti-tumor activity, presumably by altering the size distribution of KLH multimers. The KLH composition demonstrates enhanced immunogenic activity, particularly enhanced anti-tumor activity, which is reduced if the KLH is frozen or lyophilized. The KLH composition of the present invention exhibits enhanced anti-tumor activity in a murine bladder tumor model and thereby represents a new and useful anti-tumor immunotherapeutic agent.

DESCRIPTION OF THE PREFERRED EMBODIMENTS

Figure 1:
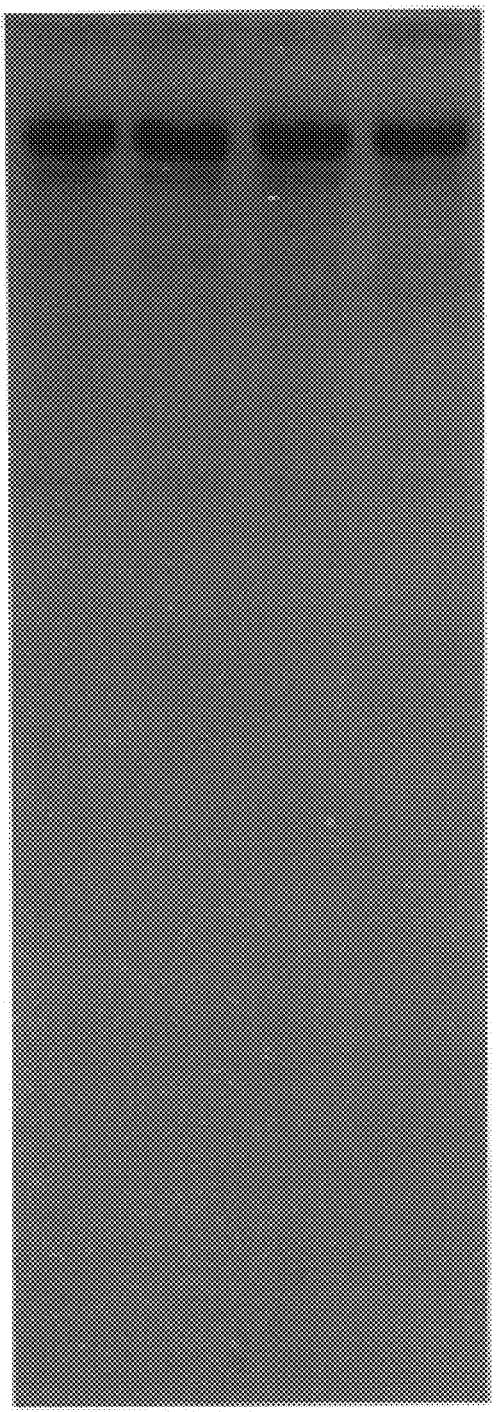
FIG. 1 shows SDS-PAGE analysis of KLH [the method of Laemmli et al. (26) under reducing conditions; 5% to 15% polyacrylamide gradient; Coomassie blue R-250 staining]. Lane 1, p-KLH; lane 2, d-KLH; lane 3, f-KLH; lane 4, l-KLH. Molecular weight markers (kDa) are shown at left.

The present invention is directed to a KLH composition which has enhanced immunogenic activity, particularly enhanced anti-tumor activity. The composition comprises KLH in a physiologically acceptable isotonic buffer. The isotonic buffer preferably contains calcium and magnesium. The KLH in the composition of the present invention comprises (i) an intact, non-degraded subunit of approximately 400,000 in molecular weight based on SDS-PAGE analysis, and (ii) at least about 50% didecameric or higher KLH multimers. The didecameric or higher KLH multimers have molecular weights of approximately 8–10 million with sedimentation coefficients of about 92–107S. The amount of didecameric or higher KLH multimers present is based on sedimentation-equilibrium and/or sedimentation-velocity ultracentrifugation analyses. It is critical that the KLH not be frozen or lyophilized at any time during the isolation, preparation or purification of the KLH or during preparation and storage of the KuH composition. The KLH composition is stored at 2°–10° C., preferably 4° C. The KLH composition is highly stable under these conditions. The concentration of KLH in the KLH composition is 0.1–20 mg/ml, preferably 2–10 mg/l, and most preferably 5 mg/ml.

The KLH composition of the present invention demonstrates an enhanced immunogenic activity, particularly enhanced anti-tumor activity. This enhanced immunogenic activity is reduced if the KLH or KLH composition is frozen or lyophilized at any time during the preparation and/or storage of KLH or the KLH composition. The enhanced immunogenic activity is seen (a) with injection of KLH (without adjuvant), (b) with KLH used as an adjuvant, (c) with KLH used as a carrier immunogen for haptens or weakly immunogenic antigens, and (d) with KLH used as an anti-tumor agent. The KLH composition of the present invention exhibits enhanced anti-tumor activity for many tumors, including but not limited to bladder tumors. The KLH composition is administered to patients with tumors in accordance with techniques known in the art, preferably by intravesical administration, after subcutaneous immunization (25) using an anti-tumor effective amount of the KLH composition. That is, in the preferred embodiment, the patient is first immunized by subcutaneous administration of the KLH composition of the present invention and then treated on a weekly basis by intravesical administration of the KLH composition.

The following abbreviations are used herein:

P-KLH is purified KLH in which the KLH is in an isotonic buffer, the KLH has not been frozen or lyophilized during the purification process, and the p-KLH is not frozen or lyophilized.

d-KLH is dissociated KLH in which the multimers existing in p-KLH have been dissociated.

f-KLH is frozen KLH in which the p-KLH was frozen for at least 24 hours.

l-KLH is lyophilized KLH in which p-KLH was lyophilized.

The KLH is purified from freshly collected hemolymph by conventional procedures. It is critical that the hemolymph and/or KLH not be frozen or lyophilized at any point during the purification of the KLH. It is also critical that the purified KLH not be frozen or lyophilized. The purified KLH is stabilized by storage in an isotonic buffer containing calcium and magnesium at about 4° C. One method suitable for purifying and storing KLH is described in Example 1 below. However, it is understood that other methods can be utilized which meet the above criteria.

The present invention is described by reference to the following Examples, which are offered by way of illustration and are not intended to limit the invention in any manner. Standard techniques well known in the art or the techniques specifically described below were utilized.

EXAMPLE 1

Purification of KLH

A saturated ammonium sulfate slurry made from freshly-collected hemolymph and containing approximately 30 mg/mL KLH was purchased from Pacific Biomarine Laboratories, Inc., Venice, Calif. The hemolymph was collected according to the guidelines of Vandenbark and associates (28): Limpets were cleaned, incised, and bled at 4° C. for approximately one hour. No massaging was done to recover additional hemolymph. KLH was precipitated by addition of solid ammonium sulfate to 65% saturation (430 g/L). The ammonium sulfate slurry was collected by centrifugation, and yielded a solution containing approximately 30–40 mg/mL protein. This solution was diluted to approximately 10–20 mg/mL with a phosphate-buffered saline (PBS) solution containing magnesium and calcium [$KH_2PO_4$ (1.5 mM), $Na_2HPO_4.7H_2O$ (8.1 mM), NaCl (136.9 mM), KCl (2.7 mM), $CaCl_2.2H_2O$ (0.9 mM), and $MgCl_2.6H_2O$ (0.5 mM); pH=7.3–7.5]. Particulates and undissolved protein were removed by centrifugation at low speed (approximately 1,000–3,000×g) for 20 min. The supernatant, which contained dissolved KLH, was centrifuged at 41,400×g for 12–18 hours. The pellet, which consisted primarily of high-molecular-weight KLH, was dissolved in PBS and recentrifuged at 41,400×g as above. The resultant pellet was again dissolved in PBS, adjusted to a final concentration of 5 mg/mL, sterilized by ultrafiltration through a microporous membrane, and stored at 40° C. This KLH solution is hereinafter referred to as purified KLH (p-KLH). KLH solution is hereinafter referred to as purified KLH (p-KLH).

It will be understood by practitioners having ordinary skill in the art that the concentrations of buffer ions and chloride salts specified in the foregoing PBS solution may be adjusted in a variety of combinations such that the ionic strength of the resultant solution remains approximately isotonic to mammalian cells. Thus, the PBS specification given above is not intended to limit the scope of the present invention, but rather to serve as a guide in the formulation of a composition that optimally preserves the immunogenicity and anti-tumor activity of KLH. It is further understood that a non-isotonic composition that nevertheless retains the important features of the present invention such as the presence of stabilizing divalent cations or pH ranges compatible with the presence of intact non-degraded KLH subunits and at least about 50% didecameric or higher multimers would be within the intended scope of the present invention.

It is of critical importance that p-KLH be protected from freezing and not be lyophilized, as these phase changes cause damage to the KLH structure and activity, as shown below.

EXAMPLE 2

Preparation of Dissociated, Frozen and Lyophilized KLH

Dissociated KLH (d-KLH) was produced by addition to p-KLH of Tris-HCl (pH 8.8) and ethylenediamine tetraacetic acid to final concentrations of 50 mM and 10 mM, respectively. Frozen (f-KLH) was prepared by placing p-KLH for at least 24 hrs in a freezer maintained at –20° C. Lyophilized KLH (l-KLH) was prepared by freeze-drying p-KLH in a Labconco® Model 75040 Freeze Dryer 8 according to the manufacturer's instructions.

EXAMPLE 3

Characterization of Non-Native, Denatured Subunit Structures by SDS-PAGE

Sodium dodecylsulfate-polyacrylamide gel electrophoresis (SDS-PAGE) was used to assess the size and purity of the KLH subunit. The results (FIG. 1) disclosed a major protein band at ≈400,000 Da, with minor protein bands, constituting <2% of the total, migrating at lower molecular weights. Since all four KLH preparations exhibited similar banding profiles, it is concluded that the processes of dissociating, freezing, or lyophilizing KLH do not affect its subunit structure. N.B. The molecular weight estimate of the KLH subunit by SDS-PAGE is known to be reliable, but anomalously low compared to estimates from other techniques such as sedimentation-equilibrium ultracentrifugation.

EXAMPLE 4

Characterization of Subunit Structures by EM

Figure 2A:
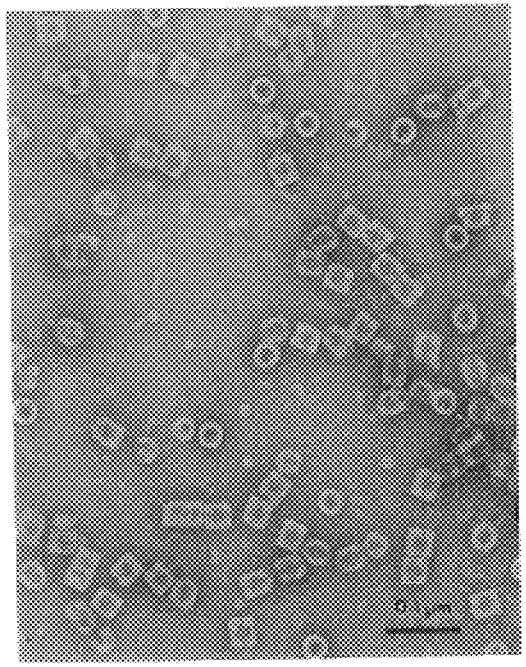
FIG. 2A shows electron microscopy of p-KLH; panel C: f-KLH; panel D: l-KLH.
Figure 2B:
FIG. 2B shows electron microscopy of d-KLH.
Figure 2C:
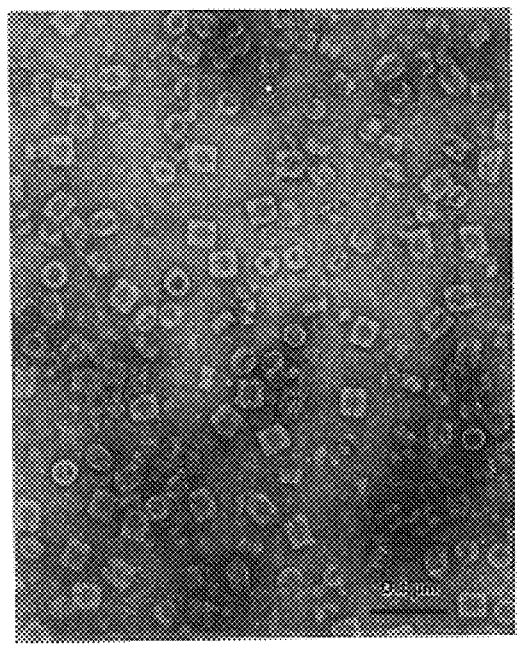
FIG. 2C shows electron microscopy of f-KLH.
Figure 2D:
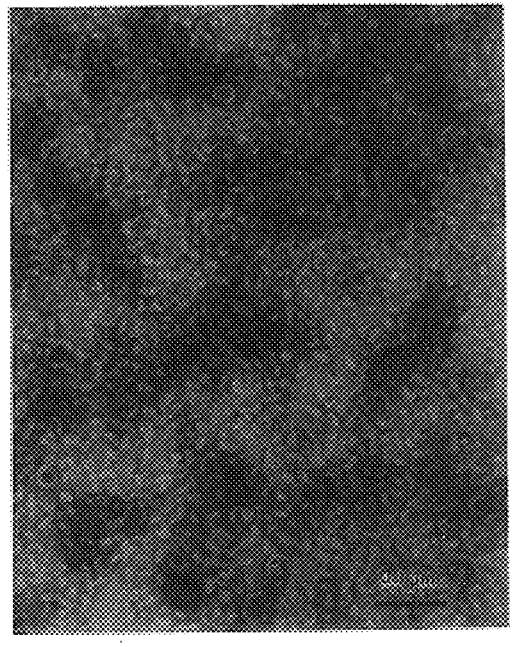
FIG. 2D shows electron microscopy of l-KLH.

Electron microscopy (EM) was used to determine the effect of dissociation, freezing, and lyophilization on KLH structure. As is evident in FIG. 2A, KLH purified according to the method of the present invention consists primarily of didecameric or higher multimers. Dissociated KLH (FIG. 2B) consists entirely of monomeric or dimeric subunits. Frozen and lyophilized KLH (FIGS. 2C and 2D) exhibit a markedly different appearance, with substantially fewer didecamers, and an increased proportion of decameric and smaller structures. That is, the f-KLH or l-KLH preparations contain substantially less than 50% didecameric or higher multimers.

EXAMPLE 5

Characterization of Native Solution Structures by Velocity Ultracentrifugation

Figure 3:
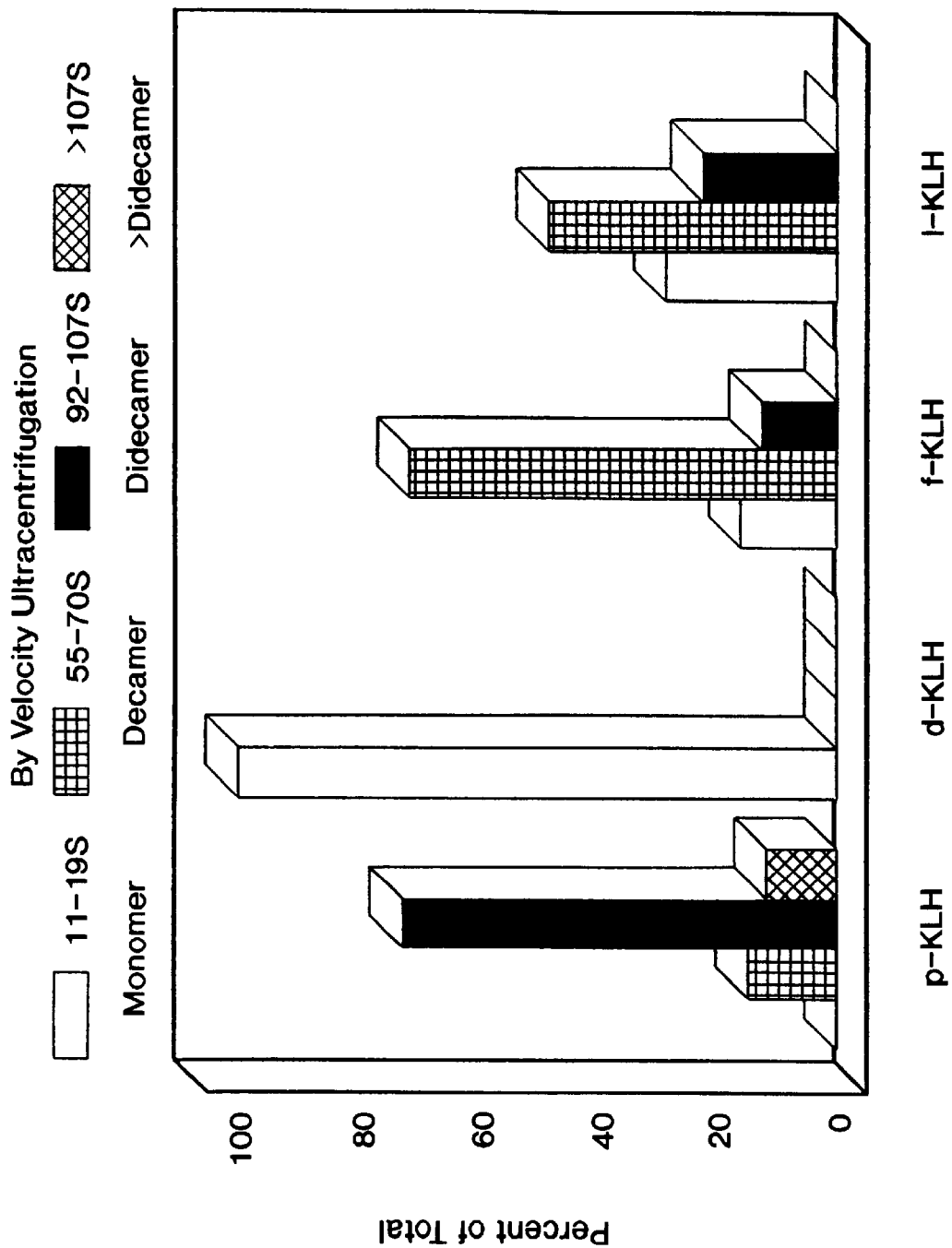
FIG. 3 shows size distribution of KLH by sedimentation-velocity ultracentrifugation. Samples were diluted 1:10 with PBS and centrifuged at 57,000×g at ambient temperature in a Beckman Model E analytical ultracentrifuge equipped with a photoelectric scanner. S values were determined by the method of Van Holde et al. (27).

Sedimentation-velocity ultracentrifugation analyses disclosed major effects of dissociating, freezing, or lyophilizing KLH on the solution structure (FIG. 3). Whereas p-KLH was found to consist of approximately 73% didecameric multimers, d-KLH, f-KLH, and l-KLH contained 0%, 13% and 23%, respectively, of this form. It also will be evident from the data in FIG. 3 that f-KLH and l-KLH exhibited a marked shift from didecameric to decameric forms that was accompanied by a substantial increase in d-KLH. Such dramatic changes in quaternary structure, merely upon freezing or lyophilization, were unexpected, and may influence the immunogenicity of the protein (see below).

EXAMPLE 6

Dose-Response Relationship of p-KLH in an Intravesical Murine Bladder Tumor Model The dose-response relationship between the amount of KLH administered and its anti-tumor effect was determined for p-KLH in the intravesical murine bladder tumor model of Shapiro et al. (29). Mice were immunized subcutaneously (footpad) with 200 µg of p-KLH three weeks prior to tumor implantation. On Day 0, mice were anesthetized (Na pentobarbital, 0.05 mg/g), catheterized, the bladder was cauterized, and $2 \times 10^4$ MB-49 bladder tumor cells (provided by G. Chodak, University of Chicago, Chicago, Ill.; 30) were instilled into the bladder in 0.1 mL of PBS. On Day 1, mice were assigned randomly to treatment groups containing 10 mice/group. On Days 1, 7, and 14, mice were anesthetized and catheterized to receive the indicated doses of p-KLH. The control group was treated s.c. (footpad) on Day -21 and intravesically on Days 1, 7, and 14 with equivalent volumes of the vehicle. The response variable in this tumor model is tumor outgrowth, which is detected by palpation and confirmed in selected animals at autopsy.

Mice were monitored for tumor outgrowth weekly for at least 4 weeks. At the end of the test period, the mice were sacrificed and the presence or absence of bladder tumors was verified macroscopically or by histological examination, as required.

Figure 4:
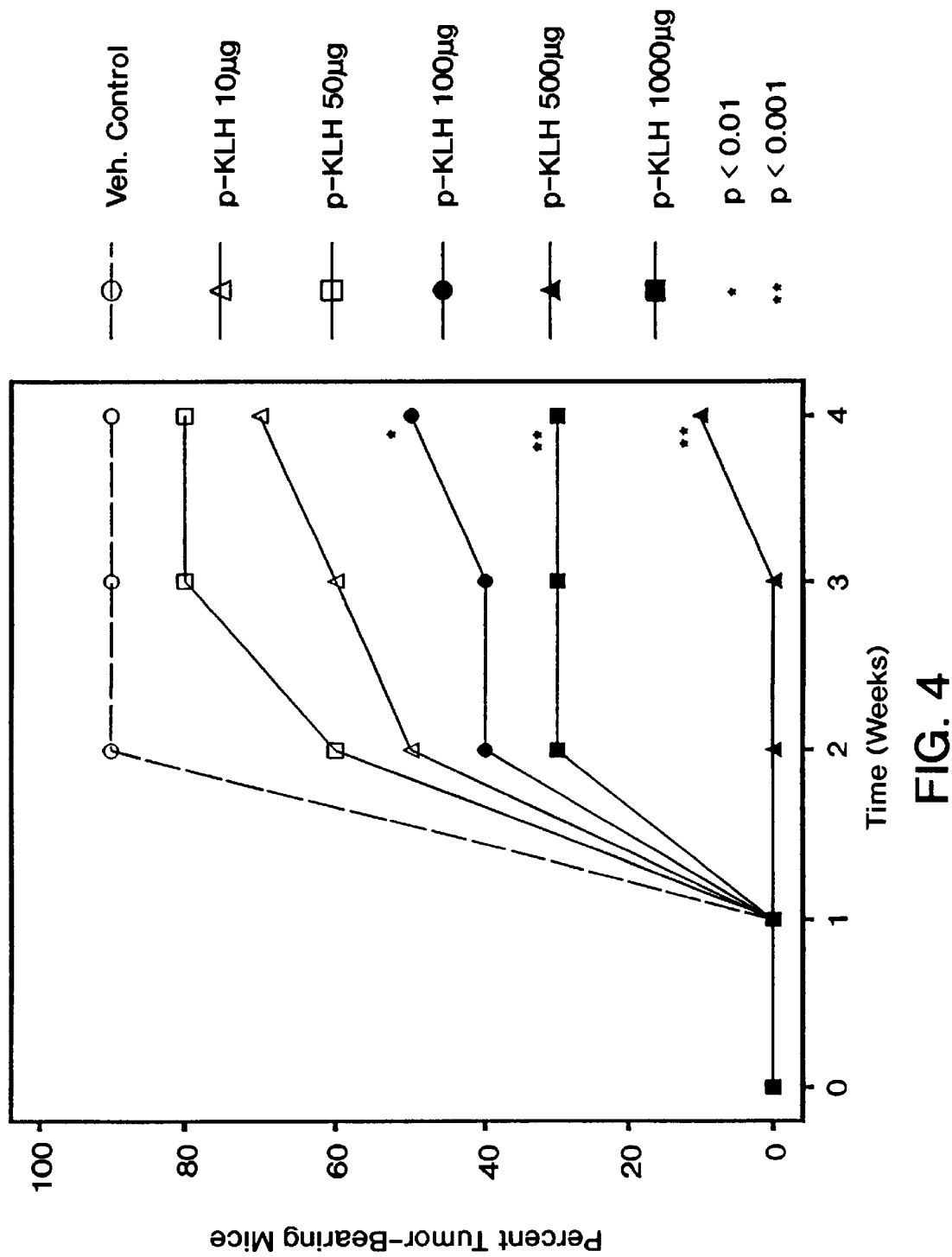
FIG. 4 shows the rate of tumor outgrowth for p-KLH in a dose-response experiment. P-KLH was given intravesically to mice inoculated on day 0 with MB-49 bladder tumor cells. ○ Vehicle control; p-KLH dosages: Δ 10 μg; □ 50 μg; ● 100 μg; ▲ 500 μg); ■ 1000 μg. * Significantly different from control (p<0.01; Fisher's Exact); ** significantly different from control (p<0.001; Fisher's Exact).

As shown in FIG. 4, there was a dose-dependent delay in tumor onset and reduction in tumor incidence among the treated groups, with maximal anti-tumor activity among groups receiving 100–1000 µg of p-KLH (the KLH composition of the present invention having enhanced immunogenic activity). At the four-week time point, significant differences (Fisher's Exact) between control vs. experimental animals were observed. Thus, 10 µg of the p-KLH composition represents a suboptimal dosage, and dosages of 100 µg or greater of the p-KLH composition are efficacious in this animal model.

EXAMPLE 7

Comparison of p-KLH, d-KLH, f-KLH and l-KLH Anti-Tumor Activity in an Intravesical Murine Bladder Tumor Model The intravesical murine bladder tumor model of Shapiro et al. (29) again was used to determine anti-tumor activity.

Two or three weeks prior to tumor implantation, female mice (6–10 weeks; 20–30 g) were immunized subcutaneously (s.c.; footpad) with p-KLH. On Day 0, the mice were anesthetized (Na-pentobarbital, 0.05 mg/g), catheterized, and bladders were cauterized and instilled with $2\times10^4$ MB-49 bladder tumor cells (30) in 0.1 mL of phosphate-buffered saline solution (PBS). On Day 1, mice were randomly sorted into groups of 10 animals each. Control animals either were immunized and treated with the vehicle (vehicle controls) or were immunized with the vehicle and treated with p-KLH (KLH controls). All experimental groups were immunized with KLH and treated either with 10 μg or 100 μg instillations. As in the previous example, the response variable in this tumor model is tumor outgrowth, which is detected by palpation and confirmed in selected animals at autopsy.

The effect of different forms of KLH administered at two dose levels was determined among the four different KIM preparations at suboptimal (10 μg) and optimal (100 μg) dosages. Two weeks prior to tumor implantation, female mice (6–10 weeks; 20–30 g) were immunized s.c. (footpad) with 200 μg of p-KLH. On Day 0, the mice were inoculated intravesically with $2\times10^4$ MB-49 bladder tumor cells as above. On Day 1, mice were randomly sorted into groups of 10 animals each. Control animals either received sham treatment with the vehicle or were sham-immunized with the vehicle and treated with KLH. Experimentals were treated either with 10 μg or 100 μg instillations of KLH from each of the four preparations.

Figure 5:
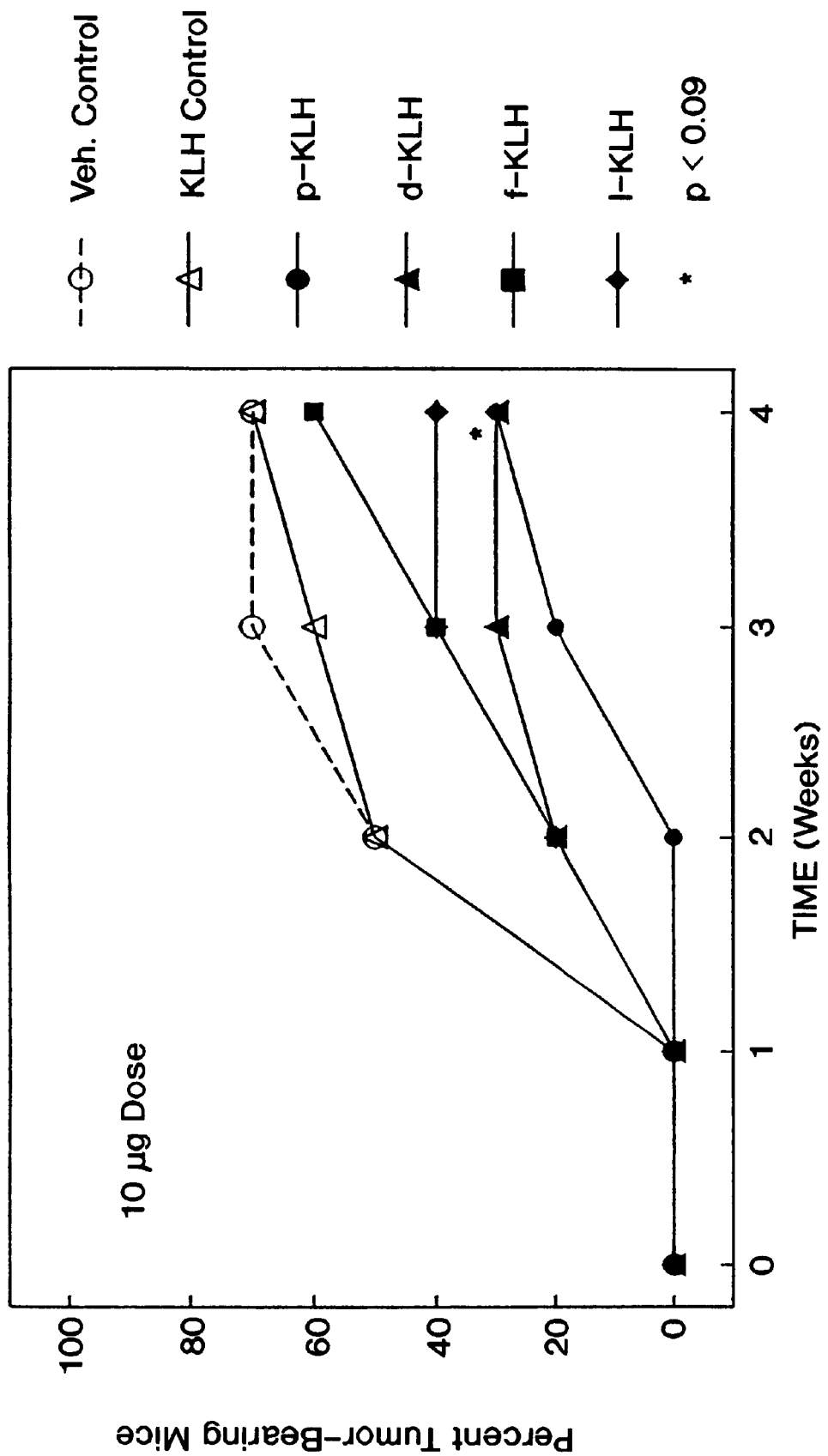
FIG. 5 shows the rate of tumor outgrowth at the 10 μg dose level. The indicated forms of KLH were given intravesically to mice inoculated on day 0 with MB-49 bladder tumor cells. ○ Vehicle control; Δ KLH control (immunized with vehicle/treated with p-KLH); ● p-KLH; ▲ d-KLH; ■ f-KLH; ♦ l-KLH. * Significantly different from control (p<0.09; Fisher's Exact).

The results for mice receiving the 10 μg dosage are summarized in FIG. 5. By four weeks post-inoculation, palpable tumors were present in 70% of mice in the vehicle or KLH-control groups. Immunized mice that were treated with 10 μg of p-KLH or d-KLH exhibited significantly fewer tumors ($p<0.09$; Fisher's Exact) than either of the control groups. Immunized mice that received f-KLH or l-KLH did not experience a significantly reduced rate of tumor outgrowth ($p>0.01$; Fisher's Exact). Maximal anti-tumor activity of a suboptimal dose of the p-KLH composition was noted, particularly at 2–4 week time points.

Figure 6:
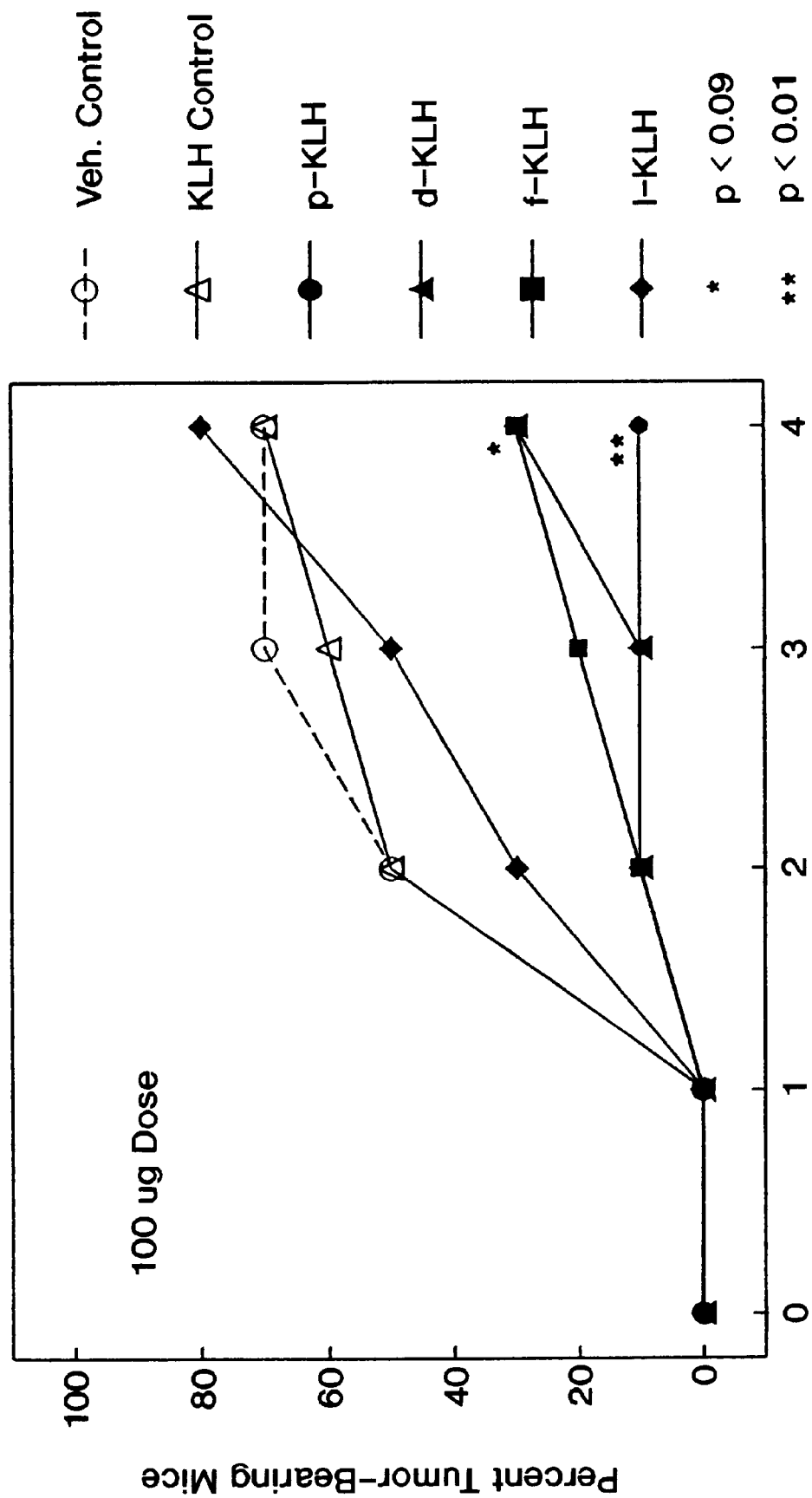
FIG. 6 shows the rate of tumor outgrowth at the 100 μg dose level. The indicated forms of KLH were given intravesically to mice inoculated on day 0 with MB-49 bladder tumor cells. ○ Vehicle control; Δ KLH control (immunized with vehicle/treated with p-KLH); ● p-KLH; ▲ d-KLH; ■ f-KLH; ♦ l-KLH. * Significantly different from control (p<0.09; Fisher's Exact).; ** significantly different from control (p<0.01; Fisher's Exact).

The results for mice receiving the 100 μg dosage are summarized in FIG. 6. By four weeks post-inoculation, palpable tumors were present in 70% of mice in the vehicle or KLH-control groups. Experimental groups that were treated with 100 μg of p-KLH exhibited significantly fewer tumors ($p<0.01$; Fisher's Exact) than either of the control groups. Immunized mice treated with dissociated or frozen KLH also experienced significantly reduced tumor outgrowth at this dosage ($p<0.09$; Fisher's Exact). Mice treated with lyophilized KLH did not experience a significantly reduced rate of tumor outgrowth ($p>0.01$; Fisher's Exact). Maximal anti-tumor activity of an efficacious dose of the p-KLH composition was noted, particularly at 2–4 week time points.

These results demonstrate that (although they retain some measure of anti-tumor activity) dissociated, frozen or lyophilized preparations of KLH are less potent than a solution of KLH that has been protected from such phase changes. Thus, the KLH composition of the present invention demonstrates enhanced immunogenic activity, particularly enhanced anti-tumor activity.

It will be appreciated that the methods and compositions of the instant invention can be incorporated in the form of a variety of embodiments, only a few of which are disclosed herein. It will be apparent to the artisan that other embodiments exist and do not depart from the spirit of the invention. Thus, the described embodiments are illustrative and should not be construed as restrictive.

LIST OF REFERENCES

1. Senozan, N. M. et al., Hemocyanin of the giant keyhole limpet, Megathura crenulata, in: "Invertebrate Oxygen-Binding Proteins", J. Lamy et al., eds., Marcel Dekker, Inc., N.Y., pp. 703–717 (1981).
2. Herscowitz, H. B. et al., Immunochemical and immunogenic properties of a purified keyhole limpet haemocyanin, Immunology 22:51–61 (1972).
3. Curtis, J. E. et al., The human primary immune response to keyhole limpet haemocyanin: Interrelationships of delayed hypersensitivity, antibody response and in vitro blast transformation, Clin. Exp. Immunol. 6:473–491 (1970).
4. Curtis, J. E. et al., The human secondary immune response to keyhole limpet haemocyanin, Clin. Exp. Immunol. 10:171–177 (1972).
5. Garvey, J. S., et al., High-molecular-weight hemocyanin. In: "Methods in Immunology", Addison-Wesley Publ. Co., pp. 135–139 (1977).
6. Herskovits, T. T. et al., Subunit structure and higher order assembly of the hemocyanins of the melongenidae family: Melonqena corona (Gmelin), Busycon canaliculatum (Linne), B. carica (Gmein), B. contrarium (Conrad), and B. spiratum (Lamarck). Comp. Biochem. Physiol. [B]94B:415–421 (1989).
7. Herskovits, T. T., Recent aspects of the subunit organization and dissociation of hemocyanins. Comp. Biochem. Physiol. 91B:597–611 (1988).
8. Herskovits, T. T. et al., Higher order assemblies of molluscan hemocyanins. Comp. Biochem. Physiol. [B]99B:19–34 (1991).
9. Savel-Niemann, A. et al., Keyhole limpet hemocyanin: On the structure of a widely used immunologic tool. In: "Invertebrate Dioxygen Carriers", G. Preaux et al., eds., Leuven University Press, Leuven, pp. 351–356 (1990).
10. Markl, J. et al., The role of two distinct subunit types in the architecture of keyhole limpet hemocyanin (KLH). Naturwiss. 78:512–514 (1991).

LIST OF REFERENCES (Cont'd)

11. Van Holde, K. E. et al., The Hemocyanins. In: "Subunits in Biological Systems", S.N. Timasheff et al., eds., Marcel Dekker, N.Y., pp. 1–53 (1971).
12. Ellerton, H. D. et al., Hemocyanin—A current perspective. Prog.Biophys.Mol.Biol. 41:143–248 (1983).
13. Silverman, D. T. et al., Epidemiology of Bladder Cancer. In: "Hematology/Oncology Clinics of North America", P.W. Kantoff et al., eds., W.B. Saunders Co., Philadelphia, p. 1 (1992).
14. Itoku, K. A. et al., Superficial Bladder Cancer. In: "Hematology/Oncology Clinics of North America", P.W. Kantoff et al., eds., W.B. Saunders Co., Philadelphia, pp. 99–116 (1992).
15. Morales, A. et al., Intracavitary bacillus Calmette-Guerin in the treatment of superficial bladder tumors. J. Urol. 116:180–183 (1976).
16. Morales, A. et al., Immunotherapy for superficial bladder cancer. A developmental and clinical overview. Urol. Clin. Nor. Am. 19:549–556 (1992).
17. Lamm, D. L., Optimal BCG treatment of superficial bladder cancer as defined by American trials. Eur. Urol. 21 Suppl. 2:12–16 (1992).
18. Olsson C. A. et al., Immunologic reduction of bladder cancer recurrence rate. J. Urol. 111:173–176 (1974).

19. Jurincic, C. D. et al., Immunotherapy in bladder cancer with keyhole-limpet hemocyanin: a randomized study. *J. Urol.* 139:723–726 (1988).
20. Flamm, J. et al., Recurrent superficial transitional cell carcinoma of the bladder: Adjuvant topical chemotherapy vs. immunotherapy. A prospective randomized trial. *J. Urol.* 144:260–263 (1990).

LIST OF REFERENCES (Cont'd)

21. Kälble, T. et al. Intravesikale rezidivprophylaze beim oberflachlichen harnblasenkarzinom mit BCG und KLH. *Urologe* 30: 118–121 (1991).
22. Flamm, J. et al., Adjuvant topical chemotherapy versus immunotherapy in primary superficial transitional cell carcinoma of the bladder. *Br. J. Urol.* 67:70–73 (1991).
23. Lamm, D. L. et al., Keyhole-limpet haemacyanin and immune ribonucleic acid immunotherapy of murine transitional cell carcinoma. *Urol. Res.* 9:227–230 (1981).
24. Lamm, D. L. et al., Immunotherapy of murine transitional cell carcinoma. *J.Urol.* 128:1104–1108 (1982).
25. Lamm, D. L. et al., Immunotherapy of murine bladder cancer with keyhole limpet hemocyanin (KLH). *J. Urol.* 149:648–652 (1993).
26. Laemmli, U. K., Cleavage of structural proteins during the assembly of the head of bacteriophage T4. *Nature* 227:680–685 (1970).
27. Van Holde, K. E. et al., Boundary analysis of sedimentation-velocity experiments with monodisperse and paucidisperse solutes. *Biopolym.* 17:1387–1403 (1978).
28. Vandenbark, A. A. et al., All KLH preparations are not created equal. *Cell.Immunol.* 60:240–243 (1981).
29. Shapiro, A., Ratliff, T. L., Oakley, D. M. and Catalona, W.J., Reduction of bladder tumor growth in mice treated with intravesical bacillus Calmette-Guerin and its correlation with bacillus Calmette-Guerin viability and natural killer cell activity. *Cancer Res.* 43:1611 (1983).
30. Chodak, G. W. and Summerhayes, I., Detection of angiogenesis activity in malignant bladder tissue and cells. *J. Urol.* 132:1032 (1984).

What is claimed is:

1. A method for treating bladder cancer which comprises administering to a patient having bladder cancer an anti-tumor effective amount of a keyhole limpet hemocyanin (KLH) composition which comprises purified KLH and a physiologically acceptable isotonic buffer, wherein said KLH comprises (i) an intact, non-degraded subunit of approximately 400,000 in molecular weight, and (ii) at least about 50% didecameric or higher multimers of said subunit.

2. The method of claim 1 wherein the concentration of KLH is about 0.1 to about 20 mg/ml.

3. The method of claim 1 wherein the concentration of KLH is about 2 to about 10 mg/ml.

4. The method of claim 1 wherein the concentration of KLH is 5 mg/ml.

5. The method of claim 1 wherein said buffer contains calcium and magnesium.

6. The method of claim 5 wherein the concentration of KLH is about 0.1 to about 20 mg/ml.

7. The method of claim 5 wherein the concentration of KLH is about 2 to about 10 mg/ml.

8. The method of claim 5 wherein the concentration of KLH is 5 mg/ml.

* * * * *